(12) United States Patent
Ota et al.

(10) Patent No.: US 10,195,095 B2
(45) Date of Patent: Feb. 5, 2019

(54) ABSORBENT ARTICLE

(71) Applicant: LIVEDO CORPORATION, Shikokuchuo-shi, Ehime (JP)

(72) Inventors: Yoshihisa Ota, Mima-gun (JP); Motoko Nishida, Mima-gun (JP)

(73) Assignee: LIVEDO CORPORATION, Shikokuchuo-shi, Ehime (JP)

( * ) Notice: Subject to any disclaimer, the term of this patent is extended or adjusted under 35 U.S.C. 154(b) by 609 days.

(21) Appl. No.: 14/782,031

(22) PCT Filed: Mar. 14, 2014

(86) PCT No.: PCT/JP2014/056848
§ 371 (c)(1),
(2) Date: Oct. 2, 2015

(87) PCT Pub. No.: WO2014/167939
PCT Pub. Date: Oct. 16, 2014

(65) Prior Publication Data
US 2016/0051423 A1    Feb. 25, 2016

(30) Foreign Application Priority Data
Apr. 11, 2013 (JP) .................. 2013-083138

(51) Int. Cl.
*A61F 13/15* (2006.01)
*A61F 13/84* (2006.01)
(Continued)

(52) U.S. Cl.
CPC .......... *A61F 13/8405* (2013.01); *A61F 13/51* (2013.01); *A61F 13/51113* (2013.01);
(Continued)

(58) Field of Classification Search
CPC .. A61F 13/8405; A61F 13/51; A61F 13/5113; A61F 2013/5107;
(Continued)

(56) References Cited

U.S. PATENT DOCUMENTS 3,707,148 A   12/1972   Bryce
4,685,909 A   8/1987    Berg et al.
(Continued)

FOREIGN PATENT DOCUMENTS

CN   102088939 A    6/2011
JP   62-28402 A     2/1987
JP   2002-505918 A  2/2002

OTHER PUBLICATIONS

Office Action dated Mar. 14, 2017, issued in counterpart Japanese Application No. 2013-083138, with English translation. (5 pages).
(Continued)

*Primary Examiner* — Jacqueline Stephens
(74) *Attorney, Agent, or Firm* — Westerman, Hattori, Daniels & Adrian (57) ABSTRACT

Absorbent article suppressing occurrence of malodor after use while preventing a rash on a wearer's skin. The absorbent article includes an absorbent body, and a fumaric acid-supported sheet disposed on a skin surface side of the absorbent body. The fumaric acid-supported sheet is a sheet which supports fumaric acid particles having an average particle diameter of 30 μm or less, and/or a sheet in which at least a part of constituent fibers is coated with fumaric acid. When being in contact with the body fluid or the like, fumaric acid is not immediately but slowly dissolved so that alkalization at the area around fumaric acid can be prevented over a long period of time. In addition, fumaric acid has an action of inhibiting proliferation of putrefactive bacteria and, therefore, can prevent occurrence of malodor from the absorbent article having absorbed the body fluid or the like.

20 Claims, 3 Drawing Sheets

(51) Int. Cl.
  *A61F 13/511*   (2006.01)
  *A61F 13/51*    (2006.01)
  *A61L 15/20*    (2006.01)
  *A61L 15/46*    (2006.01)

(52) U.S. Cl.
  CPC ............... *A61L 15/20* (2013.01); *A61L 15/46* (2013.01); *A61F 2013/51076* (2013.01); *A61F 2013/8408* (2013.01); *A61L 2300/606* (2013.01)

(58) Field of Classification Search
  CPC ....... A61F 2013/8408; A61L 2300/606; A61L 15/20; A61L 15/46
  USPC .......................................... 604/367, 359, 360
  See application file for complete search history.

(56) References Cited

U.S. PATENT DOCUMENTS

| | | | | |
|---|---|---|---|---|
| 2002/0147433 | A1* | 10/2002 | McOsker | A61L 15/42 604/364 |
| 2011/0111199 | A1 | 5/2011 | Takatori et al. | |
| 2013/0065765 | A1* | 3/2013 | Selifonov | C08F 8/14 504/361 |
| 2015/0297424 | A1* | 10/2015 | Ota | A61L 15/60 604/372 |

OTHER PUBLICATIONS

International Search Report dated Jun. 3, 2014, issued in counterpart applicaiton No. PCT/JP2014/056848 (2 pages).

\* cited by examiner

ABSORBENT ARTICLE

FIELD OF THE INVENTION

The present invention relates to an absorbent article, particularly relates to an absorbent article preventing rash on a wearer's skin and suppressing an odor from the absorbent article after absorbing body fluid.

DESCRIPTION OF THE RELATED ART

Absorbent articles such as disposable diapers, sanitary napkins, and incontinence pads are usually employed in a manner that a top sheet thereof directly contacts the wearer's skin. Accordingly the top sheet becomes alkaline by the body fluid such as the excreted urine and the excreted menstrual blood, resulting in an environment where sebum, and membrane composed of protein or amino acid of the wearer's skin easily flow away, and therefore, rash easily occurs on the wearer's skin.

An absorbent article for preventing such rash has been proposed so far. For example, Patent literature 1 discloses a disposable absorbent article useful for absorbing the excreted body fluid while also preventing or reducing diaper rash, said absorbent article comprising: (A) a liquid impervious backing sheet; (B) a relatively hydrophobic and liquid pervious top sheet, said top sheet comprising therein or thereon at least one pH adjusting agent suitable for maintaining skin pH within a range from about 3.0 to 5.5 in the presence of urea; and (C) a flexible absorbent core positioned between said backing sheet and said top sheet (said flexible absorbent core comprising an essentially hydrophilic fiber material, and particles of a substantially water-insoluble and highly neutralized hydrogel material having at least 50% of its acidic functional groups neutralized with a salt-forming cation) (refer to (claim 7) of Patent literature 1).

CITATION LIST

Patent Literature

Patent literature 1: Japanese Patent Publication No. S62-28402 A

SUMMARY OF THE INVENTION

Problems to be Solved

Patent literature 1 exemplifies organic acids such as citric acid, adipic acid, and fumaric acid as the pH adjusting agent (line 18 of left-lower column to line 3 of right-lower column on page 9, Patent literature 1). However, the water-soluble compound such as citric acid is easily dissolved and dispersed into the body fluid, so the water-soluble compound cannot be retained in body fluid discharged portions (urine excreting portion, and menstrual blood excreting portion). As a result, weak acidity cannot be maintained in the body fluid discharged portions contacting the wearer and thus the rash-preventing effect is not obtained. In addition, Patent literature 1 does not actually employ the water-insoluble pH adjusting agent such as fumaric acid, and fails to discuss supporting property of such water-insoluble compound.

In addition, in the used absorbent article, putrefactive bacteria easily proliferate in the body fluid, and malodor is sometimes given off after a period of time. However, no sufficient measures have been taken against occurrence of the malodor caused by such putrefactive bacteria.

The present invention has been made in view of the above circumstances, and an objective of the present invention is to provide an absorbent article suppressing occurrence of malodor after absorbing body fluid as well as preventing rash on a wearer's skin.

Solutions for Solving the Problems

The absorbent article according to the present invention comprises an absorbent body, and a fumaric acid-supported sheet disposed on a skin surface side of the absorbent body, wherein the fumaric acid-supported sheet is a sheet which supports fumaric acid particles having an average particle diameter of 30 μm or less, and/or a sheet in which at least a part of constituent fibers is coated with fumaric acid. When being in contact with the body fluid or the like, the water-insoluble fumaric acid is not immediately but slowly dissolved into the body fluid or the like. Therefore, if a fumaric acid-supported sheet is disposed, alkalization by the body fluid can be prevented on and around the fumaric acid-supported sheet over a long period of time. If the fumaric acid-supported sheet has fumaric acid particles having an average particle diameter of 30 μm or less, fumaric acid particles are easily supported by a supporting member (e.g. a sheet material), and hardly detach from the supporting member. Further, if the constituent fibers are coated with fumaric acid, fumaric acid hardly detaches from the constituent fibers. Accordingly, by disposing the fumaric acid-supported sheet at the position being in contact with the body fluid and the like of the absorbent article, the rash can be suppressed over a long period of time. In addition, fumaric acid has an action of inhibiting proliferation of putrefactive bacteria. As a result, disposing the fumaric acid-supported sheet at the position (e.g. portion around the water absorbent resin powder) being in contact with the body fluid and the like of the absorbent article prevents occurrence of malodor from the absorbent article after having absorbed the body fluid or the like.

It is preferred that at least a part of a particle surface of the fumaric acid particles is coated with a dispersant. The fumaric acid-supported sheet preferably supports fumaric acid in a supporting amount ranging from 0.01 g/m$^2$ to 10 g/m$^2$. The dispersant is preferably at least one selected from the group consisting of an anionic high molecular type dispersant, an anionic surfactant type dispersant, and a nonionic surfactant type dispersant.

Preferred examples of the embodiment of the absorbent article include an embodiment where the absorbent article comprises a top sheet disposed on a skin surface side of the absorbent body, and a back sheet disposed on an external surface side of the absorbent body, and the top sheet is the fumaric acid-supported sheet; and an embodiment where the absorbent article comprises a top sheet disposed on a skin surface side of the absorbent body, a back sheet disposed on an external surface side of the absorbent body, and an intermediate sheet disposed between the absorbent body and the top sheet, wherein the intermediate sheet is the fumaric acid-supported sheet. It is preferred that the fumaric acid-supported sheet is obtained by contacting a sheet base material with a fumaric acid-containing liquid containing fumaric acid and a solvent, and then removing the solvent for the sheet base material to support fumaric acid. The fumaric acid-containing liquid preferably contains a dispersant.

Technical Effect

According to the absorbent article of the present invention, occurrence of malodor after absorbing the body fluid can be suppressed as well as the rash on the wearer's skin can be prevented.

DESCRIPTION OF THE PREFERRED EMBODIMENT

The absorbent article according to the present invention comprises an absorbent body, and a fumaric acid-supported sheet disposed on a skin surface side of the absorbent body, wherein the fumaric acid-supported sheet is a sheet which supports fumaric acid particles having an average particle diameter of 30 µm or less, and/or a sheet in which at least a part of constituent fibers is coated with fumaric acid. Fumaric acid has a solubility (25° C.) of 0.63 g/100 g in water, thus it is water-insoluble. Such fumaric acid, when being in contact with the body fluid or the like, is not immediately but slowly dissolved. Fumaric acid has two carboxylic groups in its molecule, thus exhibits acidity in a fluid. Therefore, if the fumaric acid-supported sheet is disposed at the position being in contact with the body fluid and the like of the absorbent article, alkalization by the body fluid and the like can be prevented on and around the fumaric acid-supported sheet over a long period of time. If the fumaric acid-supported sheet has fumaric acid particles having an average particle diameter of 30 µm or less, the fumaric acid particles are easily supported by a supporting member (e.g. a sheet material such as a nonwoven fabric), and detachment thereof from the supporting member can also be suppressed. Further, if the constituent fibers are coated with fumaric acid, fumaric acid hardly detaches from the constituent fibers. As a result, disposing the fumaric acid-supported sheet to the absorbent article, the rash on the wearer's skin can be suppressed over a long period of time. In addition, fumaric acid has an action of inhibiting proliferation of putrefactive bacteria. As a result, disposing the fumaric acid-supported sheet at the portion around the water absorbent resin powder in which the body fluid and the like are retained, occurrence of malodor from the absorbent article after having absorbed the body fluid or the like can be prevented. The position where the fumaric acid-supported sheet is disposed may be any position that can be in contact with the body fluid to be absorbed in the absorbent article, and the fumaric acid-supported sheet is preferably disposed on a side which is closer to the skin surface than the absorbent body and will be described later.

Examples of the fumaric acid-supported sheet employed in the present invention include a sheet which supports fumaric acid particles having an average particle diameter of 30 µm or less; and a sheet in which at least a part of constituent fibers is coated with fumaric acid. Examples of the sheet base material of the fumaric acid-supported sheet include a liquid permeable sheet material such as a nonwoven fabric. Examples of the nonwoven fabric include a point-bonded nonwoven fabric, an air-through nonwoven fabric, a spunlace nonwoven fabric, and a spunbond nonwoven fabric. Examples of the fiber forming these nonwoven fabric include a hydrophilic fiber such as cellulose, rayon and cotton; a hydrophobic fiber such as polypropylene, polyethylene, polyester, polyamide and nylon; and a hydrophobic fiber whose surface is hydrophilized with a surfactant.

Examples of the sheet supporting the fumaric acid particles include a nonwoven fabric in which the constituent fibers thereof support the fumaric acid particles. The fumaric acid particles used for the sheet supporting the fumaric acid particles have an average particle diameter of 30 µm or less, preferably have an average particle diameter of 25 µm or less, and more preferably have an average particle diameter of 20 µm or less. If the average particle diameter is 30 µm or less, the fumaric acid particles are easily supported by the sheet material such as a nonwoven fabric, and detachment thereof from the sheet material can also be suppressed. The lower limit of the average particle diameter of the fumaric acid particles is not particularly limited, but the lower limit is preferably 0.05 µm. It is noted that, in the present invention, the average particle diameter of the fumaric acid particles can be measured with a laser diffraction scattering type particle size analyzer before the fumaric acid particles are supported by the sheet base material. In addition, in the case of supporting the fumaric acid particles by contacting the sheet base material with a fumaric acid particle dispersion liquid, which is described later, the average particle diameter of the fumaric acid particles in the fumaric acid particle dispersion liquid is deemed as the average particle diameter of the fumaric acid particles supported by the fumaric acid-supported sheet. The average particle diameter of the fumaric acid particles in the fumaric acid particle dispersion liquid can be measured with a laser diffraction scattering type particle size analyzer. In the present invention, the average particle diameter of the fumaric acid particles is a volume-based average particle diameter.

It is preferred that at least a part of a particle surface of the fumaric acid particles is coated with a dispersant. If at least a part of the particle surface of the fumaric acid particles is coated with the dispersant, the dispersant functions as a binder for binding the fumaric acid particles and the sheet base material. As a result, the fumaric acid particles more firmly retain on the supporting member, and detachment thereof from the sheet base material further decreases. Further, in the case of supporting the fumaric acid particles by applying the fumaric acid particle dispersion liquid to the sheet base material as described later, if the dispersant is added in the dispersion liquid, the fumaric acid particles can be dispersed more uniformly. The coating of the fumaric acid particles with the dispersant can be conducted by mixing the fumaric acid particles, the dispersant and a solvent, and then removing the solvent.

The dispersant is not particularly limited, as long as it has an effect of improving dispersibility of the fumaric acid particles in the dispersion liquid, and examples thereof include an high molecular type dispersant, and an surfactant type dispersant. The high molecular type dispersant and the surfactant type dispersant include an anionic dispersant, a nonionic dispersant, and a cationic dispersant, respectively, among them, the anionic dispersant or nonionic dispersant is preferred.

The high molecular type dispersant exhibits repulsion effect due to the steric hindrance of the dispersant molecules, thus has excellent dispersion stability over a long period of time. Further, the high molecular type dispersant excellently functions as a binder for binding the fumaric acid particles and the supporting member. The weight average molecular weight of the high molecular type dispersant is preferably 1,000 or more, and is preferably 200,000 or less, more preferably 100,000 or less.

Examples of the anionic high molecular type dispersant include a polycarboxylic acid (salt) type dispersant, a polysulfonic acid type dispersant, and the like. Examples of the polycarboxylic acid (salt) type dispersant include an unsaturated carboxylic acid polymer or copolymer (e.g. polyacrylic acid, isobutylene-maleic acid copolymer, diisobutylene-maleic acid copolymer, styrene-maleic acid copolymer, styrene-maleic acid-(meth)acrylic acid ester copolymer, and (meth)acrylic acid-(meth)acrylic acid ester copolymer), a carboxylated polysaccharide (e.g. carboxymethyl cellulose), and salts thereof (e.g. organic amine salt, alkaline metal salt, alkaline earth metal salt). Examples of the polysulfonic acid type dispersant include a naphthalenesulfonic acid formalin condensate, polystyrenesulfonic acid, and salts thereof (e.g. organic amine salt, alkaline metal salt, alkaline earth metal salt). Examples of the nonionic high molecular type dispersant include polyvinyl alcohol, polyethylene glycol, and the like. Examples of the cation high molecular type dispersant include an inorganic acid (e.g. hydrochloric acid, phosphoric acid) salt or an organic acid (e.g. formic acid, acetic acid, lactic acid) salt of a N,N-dialkylaminoalkyl(meth)acrylate polymer or copolymer. In addition, the alkyl group bonding to the nitrogen atom in the N,N-dialkylaminoalkyl (meth) acrylate polymer or copolymer preferably has 1 to 3 carbon atoms, and the alkylene group preferably has 2 or 3 carbon atoms.

The surfactant type dispersant is adsorbed to the surface of the fumaric acid particles, and improves the wettability of the fumaric acid particles to the solvent. The weight average molecular weight of the surfactant type dispersant is preferably 100 or more, and is preferably 10,000 or less.

Examples of the anionic surfactant type dispersant include a carboxylic acid (salt) type dispersant, a sulfonic acid (salt) type dispersant, a sulfuric acid ester salt, and the like. Examples of the carboxylic acid (salt) type dispersant include a salt of a fatty acid having 6 to 15 carbon atoms (e.g. organic amine salt, alkaline metal salt, alkaline earth metal salt). Examples of the sulfonic acid (salt) type dispersant include dialkylsulfosuccinate (e.g. organic amine salt, alkaline metal salt, alkaline earth metal salt). The alkyl group in dialkylsulfosuccinate preferably has 6 to 15 carbon atoms. Examples of the sulfuric acid ester salt include polyoxyalkylenealkyl ether sulfate (e.g. organic amine salt, alkaline metal salt, alkaline earth metal salt), and polyoxyalkylenealkylphenyl ether sulfate (e.g. organic amine salt, alkaline metal salt, alkaline earth metal salt). In polyoxyalkylenealkyl ether sulfate and polyoxyalkylenealkylphenyl ether sulfate, the alkylene group preferably has 2 to 4 carbon atoms, and the alkyl group preferably has 1 to 20 carbon atoms. Examples of the nonionic surfactant type dispersant include a polyoxyalkylene type dispersant, and a polyhydric alcohol type dispersant. Examples of the polyoxyalkylene type dispersant include polyoxyalkylenealkyl ether, polyoxyalkylene fatty acid ester, polyoxyalkylene polyhydric alcohol fatty acid ester, polyoxyalkylenealkylphenyl ether, polyoxyalkylenealkylamino ether, and polyoxyethylene-propylene block polymer. Examples of the polyhydric alcohol type dispersant include polyhydric alcohol fatty acid ester, polyhydric alcohol alkylester ether, and fatty acid dialkylolamide. Examples of the cation surfactant type dispersant include a quaternary ammonium type dispersant.

Among them, as the dispersant, the anionic high molecular type dispersant, the anionic surfactant type dispersant, and the nonionic surfactant type dispersant are preferred, the anionic high molecular type dispersant is more preferred, and the polycarboxylic acid (salt) type dispersant is particularly preferred.

If the polycarboxylic acid (salt) type dispersant is employed, aggregate of the fumaric acid particles can be more easily broken and ground down by friction in the fumaric acid particle dispersion liquid due to the mechanical operation. Further, an electric bilayer is formed due to dissociation of the polycarboxylic acid (salt) adsorbed on the particle surface, thus reaggregation of the fumaric acid particles is inhibited by the electric repulsion. As a result, the fumaric acid particles show better dispersion stability in the fumaric acid particle dispersion liquid.

Specific examples of the polycarboxylic acid (salt) type dispersant include: "CARRYBON (registered trademark) B", "CARRYBON L-400", "CARRYBON AR-33", "SAN-SPEARL (registered trademark) PS-8", and "GRANUP (registered trademark) PC-121" commercially available from Sanyo Chemical Industries Co. Ltd.; "UTC-124" commercially available from Takemoto Oil & Fat Co. Ltd.; "Shallol (registered trademark) AN-103P", and "Shallol AN-144P" commercially available from DKS Co. Ltd.; "Thickener A-818" commercially available from San Nopco Limited; and the like.

The amount of the dispersant is preferably 1 part by mass or more, more preferably 2 parts by mass or more, even more preferably 5 parts by mass or more, and is preferably 50 parts by mass or less, more preferably 45 parts by mass or less, even more preferably 40 parts by mass or less, with respect to 100 parts by mass of the fumaric acid particles. If the amount of the dispersant falls within the above range, the fumaric acid particles show enhanced dispersion stability. On the other hand, even if the amount of the dispersant exceeds 50 parts by mass, since the improvement in the dispersion stability is confirmed no longer, it is economically disadvantageous. Furthermore, since the viscosity of the dispersion increases, the processing efficiency tends to deteriorate.

Examples of the sheet in which at least a part of the constituent fibers thereof is coated with fumaric acid include a nonwoven fabric in which at least a part of the constituent fibers thereof is coated with fumaric acid. In the case that the constituent fibers are coated with fumaric acid, the employed fiber is not particularly limited, and a fiber having a polar group (such as a hydroxyl group, ester group, and ether group) is preferred. It is considered that if the fiber having the polar group is employed as the fiber, coating becomes easier due to hydrogen bond. In addition, if fumaric acid is coated on the fiber by the method of contacting the sheet base material and the fumaric acid liquid as described later, even a hydrophobic fiber is employed, coating is also easy. In the case that the constituent fibers are coated with fumaric acid, the thickness of fumaric acid coating the fiber is preferably 0.1 µm or less.

The supporting amount of fumaric acid on the fumaric acid-supported sheet is preferably 0.01 $g/m^2$ or more, more preferably 0.02 $g/m^2$ or more, even more preferably 0.03 $g/m^2$ or more, and is preferably 10 $g/m^2$ or less, more preferably 5.0 g/m² or less, even more preferably 4.5 g/m² or less, particularly preferably 4.0 g/m² or less. If the supporting amount falls within the above range, skin stimulation suppression effect and malodor suppression effect further increase. The supporting amount of fumaric acid is determined by Soxhlet extracting a fumaric acid-supported sheet that is cut into a determined size (e.g. 1 cm²) using a large quantity of ethanol (e.g. 2 L) to completely dissolve the supported fumaric acid, and then measuring the mass of fumaric acid in the solution. In addition, in the case of spraying the fumaric acid-containing liquid on the sheet base material as described later, the supporting amount of fumaric acid can also be determined based on the concentration of the fumaric acid in the fumaric acid-containing liquid and the sprayed liquid amount.

The ratio (supporting amount of fumaric acid/mass per unit area of water absorbent resin powder) of the supporting amount of fumaric acid on the fumaric acid-supported sheet to the mass per unit area of the water absorbent resin powder in the absorbent article which will be described later, is preferably 0.001 or more, more preferably 0.002 or more, even more preferably 0.003 or more, and is preferably 20 or less, more preferably 18 or less, even more preferably 16 or less. If the ratio falls within the above range, skin stimulation suppression effect and malodor suppression effect further increase.

The fumaric acid-supported sheet may be obtained by making the fumaric acid particles being supported by the sheet base material, or by coating the fibers constituting the sheet base material with fumaric acid. The method of manufacturing the fumaric acid-supported sheet is not particularly limited, and examples thereof include: a method of spreading the powder of the fumaric acid particles on the supporting member; and a method of contacting the sheet base material with the fumaric acid-containing liquid containing fumaric acid and a solvent, and then removing the solvent. Examples of the method of making the fumaric acid particles being supported by the sheet base material include: a method of spraying the dispersion liquid containing the fumaric acid particles on the supporting member, and then removing the solvent; a method of immersing the supporting member in the dispersion liquid containing the fumaric acid particles, and then removing the solvent; and the like. Examples of the method of coating the fibers constituting the sheet base material with fumaric acid include: a method of spraying the fumaric acid solution in which fumaric acid is dissolved on the supporting member, and then removing the solvent; a method of immersing the supporting member in the fumaric acid solution in which fumaric acid is dissolved, and then removing the solvent; and the like. When the absorbent article is manufactured, the fumaric acid-supported sheet which has been prepared in advance may be used as the top sheet, the intermediate sheet or the like. Further, when the absorbent article is manufactured, the sheet base material on which no fumaric acid is supported may be disposed as the top sheet, the intermediate sheet or the like, and then the fumaric acid-containing liquid is sprayed on the sheet base material.

The content of fumaric acid in the fumaric acid-containing liquid is preferably 0.05 mass % or more, more preferably 0.10 mass % or more, even more preferably 0.15 mass % or more, and is preferably 50 mass % or less, more preferably 47 mass % or less, even more preferably 45 mass % or less. If the content of fumaric acid falls within the above range, supporting property on the supporting member further increases The fumaric acid-containing liquid preferably contains the above-described dispersant. The content of dispersant in the fumaric acid-containing liquid is preferably 1 part by mass or more, more preferably 2 parts by mass or more, even more preferably 5 parts by mass or more, and is preferably 50 parts by mass or less, more preferably 45 parts by mass or less, even more preferably 40 parts by mass or less, with respect to 100 parts by mass of fumaric acid. If the content of dispersant falls within the above range, the fumaric acid particles show enhanced dispersion stability. On the other hand, even if the amount of the dispersant exceeds 50 parts by mass, since the improvement in the dispersion stability is confirmed no longer, it is economically disadvantageous. Furthermore, since the viscosity of the dispersion increases, the processing efficiency tends to deteriorate.

As the solvent of the fumaric acid-containing liquid, water, a mixed solvent of water and a hydrophilic organic solvent, or the like can be used. Examples of the hydrophilic organic solvent include methanol, ethanol, acetone, glycerin, ethylene glycol, propylene glycol, and the like. Examples of the method of removing the solvent include a method of evaporating the solvent after contacting the dispersion liquid with the supporting member.

The absorbent article according to the present invention comprises an absorbent body absorbing the body fluid. The absorbent body comprises at least one absorbent layer. The absorbent layer preferably includes the water absorbent resin powder as a water absorbent material. The absorbent layer may further includes a water absorbent fiber as the water absorbent material. Examples of the water absorbent fiber include a pulp fiber, a cellulose fiber, and rayon. The absorbent layer may further include a fiber base material in addition to the water absorbent resin powder. Examples of the fiber base material include a thermal bonding fiber, and the like. The thermal bonding fiber is used to enhance shape retention. Specific examples of the thermal bonding fiber include a polyolefin fiber such as a polyethylene fiber and a polypropylene fiber; a polyester fiber; and a composite fiber. If the absorbent layer includes the water absorbent material consisting of the water absorbent resin powder, a thin type absorbent layer becomes possible. If the absorbent layer further includes the fiber base material, the body fluid disperse better therein.

The absorbent layer may be obtained, for example, by fixing a mixture which is obtained by mixing the particulate water absorbent resin powder in a hydrophilic fiber assembly layer composed of pulverized pulp fibers, cellulose fibers or the like, to a paper sheet such as a tissue paper or to a liquid permeable; or by wrapping the above-described mixture with a liquid permeable nonwoven fabric sheet, and molding into a desired shape such as a rectangular shape, an hourglass shape, a gourd shape, a battledore shape, or the like.

The water absorbent resin powder used in the present in the present invention is not particularly limited, and (A) a crosslinked polymer mainly composed of acrylic acid and having carboxyl groups thereof being at least partially neutralized is preferably used. The content of the acrylic acid component forming (A) the crosslinked polymer is preferably 90 mass % or more, more preferably 95 mass % or more, and is preferably 99 mass % or less, more preferably 97 mass % or less. If the content of the acrylic acid component falls within the above range, the obtained water absorbent resin powder can easily exhibit a desired absorption performance.

Examples of the cation for neutralizing at least a part of the carboxyl groups of (A) the crosslinked polymer include, but not particularly limited to, an alkali metal ion such as lithium, sodium, and potassium; and an alkaline earth metal ion such as magnesium and calcium. The neutralization degree of the carboxyl groups of the crosslinked polymer is preferably 60 mole % or more, and more preferably 65 mole % or more. This is because the absorption performance of the obtained water absorbent resin powder may deteriorate if the neutralization degree is excessively low. Furthermore, there is no particular limitation on the upper limit of the neutralization degree, and all the carboxyl groups may be neutralized. It is noted that the neutralization degree is obtained according to the following formula.

> Neutralization degree (mole %)=100×[Number of moles of the neutralized carboxyl groups in the crosslinked polymer]/[Total number of moles of the carboxyl groups in the crosslinked polymer (including neutralized and unneutralized carboxyl groups)]

The crosslinked polymer is preferably obtained by polymerizing an unsaturated monomer composition containing (a1) a water-soluble ethylenically unsaturated monomer and/or (a2) a hydrolyzable monomer producing (a1) the water-soluble ethylenically unsaturated monomer by hydrolysis; and (b) an internal crosslinking agent.

As (a1) the water-soluble ethylenically unsaturated monomer, for example, a monomer having at least one water-soluble substituent and an ethylenically unsaturated group, or the like can be used. The water-soluble monomer means a monomer having a property of being dissolved at least in an amount of 100 g in 100 g of water at 25° C. In addition, (a2) the hydrolyzable monomer is hydrolyzed with water at 50° C., by the action of a catalyst (an acid, a base, or the like) where necessary, to produce (a1) the water-soluble ethylenically unsaturated monomer. The hydrolysis of (a2) the hydrolyzable monomer may be conducted during, after, or both during and after the polymerization of the crosslinked polymer. However, in light of the molecular weight of the obtained water absorbent resin powder, the hydrolysis of (a2) the hydrolyzable monomer is preferably conducted after the polymerization of the crosslinked polymer.

Examples of the water-soluble substituent include a carboxyl group, sulfo group, sulfoxy group, phosphono group, hydroxyl group, carbamoyl group, amino group, salts thereof, and an ammonium salt. The salt of the carboxyl group (carboxylate), the salt of the sulfo group (sulfonate), and the ammonium salt are preferred. In addition, examples of the salt include a salt of alkali metal such as lithium, sodium, and potassium; and a salt of alkaline earth metal such as magnesium and calcium. The ammonium salt may be any of salts of primary to tertiary amines or a quaternary ammonium salt. Among these salts, in light of absorption properties, the alkali metal salt and ammonium salt are preferred, the alkali metal salt is more preferred, and the sodium salt is further preferred.

As the water-soluble ethylenically unsaturated monomer having the carboxyl group and/or the salt thereof, an unsaturated carboxylic acid having 3 to 30 carbon atoms and/or a salt thereof is preferred. Specific examples of the water-soluble ethylenically unsaturated monomer having the carboxyl group and/or the salt thereof include an unsaturated monocarboxylic acid and/or a salt thereof such as (meth) acrylic acid and (meth)acrylic acid salt; an unsaturated dicarboxylic acid and/or a salt thereof such as maleic acid and maleate; and a monoalkyl ester of an unsaturated dicarboxylic acid and/or a salt thereof such as maleic acid monobutyl ester. It is noted that in the description of the present invention, "(meth) acrylic" means "acrylic" and/or "methacrylic". Examples of a water-soluble ethylenically unsaturated monomer having the sulfo group and/or the salt thereof include vinyl sulfonic acid, styrene sulfonic acid, and the like.

(a2) The hydrolyzable monomer is not particularly limited, and an ethylenically unsaturated monomer having at least one hydrolyzable substituent that becomes a water-soluble substituent by hydrolysis is preferred. Examples of the hydrolyzable substituent include a group containing an acid anhydride, a group containing an ester bond, and a cyano group. Examples of the ethylenically unsaturated monomer having the group containing the acid anhydride include an unsaturated dicarboxylic anhydride having 4 to 20 carbon atoms, and the like. Examples of the ethylenically unsaturated monomer having the group containing the ester bond include a lower alkyl ester of an ethylenically unsaturated carboxylic acid and an ester of an ethylenically unsaturated alcohol. Examples of the ethylenically unsaturated monomer having the cyano group include a nitrile compound containing a vinyl group such as (meth) acrylonitrile.

As each of (a1) the water-soluble ethylenically unsaturated monomer and (a2) the hydrolyzable monomer, a single monomer or a mixture of two or more monomers may be used. The same applies to the case where (a1) the water-soluble ethylenically unsaturated monomer and (a2) the hydrolyzable monomer are used in combination.

As the monomer constituting (A) the crosslinked polymer, in addition to (a1) the water-soluble ethylenically unsaturated monomer and (a2) the hydrolyzable monomer, (a3) other vinyl monomer that is copolymerizable with these monomers can be used. As (a3) the other vinyl monomer, a hydrophobic vinyl monomer and the like can be used, but it is not limited thereto. In light of absorption properties, the content of (a3) the other vinyl monomer is most preferably 0 mole %.

Examples of (b) the internal crosslinking agent include: (b1) an internal crosslinking agent having two or more ethylenically unsaturated groups; (b2) an internal crosslinking agent having at least one ethylenically unsaturated group, and at least one functional group that can react with the water-soluble substituent of (a1) the water-soluble ethylenically unsaturated monomer and/or the water-soluble substituent produced by hydrolysis of (a2) the hydrolyzable monomer; and (b3) an internal crosslinking agent having at least two functional groups that can react with the water-soluble substituent of (a1) the water-soluble ethylenically unsaturated monomer and/or the water-soluble substituent produced by hydrolysis of (a2) the hydrolyzable monomer.

Examples of (b1) the internal crosslinking agent include a bis(meth)acrylamide having 8 to 12 carbon atoms, a poly(meth)acrylate of a polyol having 2 to 10 carbon atoms, a polyallylamine having 2 to 10 carbon atoms, and a poly(meth)allyl ether of a polyol having 2 to 10 carbon atoms. Specific examples thereof include N,N'-methylene bis(meth)acrylamide, ethylene glycol di(meth)acrylate, poly (polymerization degree of 2 to 5) ethylene glycol di(meth) acrylate, propylene glycol di(meth)acrylate, glycerin (di or tri) acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth)acrylate.

Examples of (b2) the internal crosslinking agent include an ethylenically unsaturated compound having 6 to 8 carbon atoms and an epoxy group, an ethylenically unsaturated compound having 4 to 8 carbon atoms and a hydroxyl group, and an ethylenically unsaturated compound having 4 to 8 carbon atoms and an isocyanate group.

Examples of (b3) the internal crosslinking agent include a polyhydric alcohol, a polyvalent glycidyl, a polyvalent amine, a polyvalent aziridine, and a polyvalent isocyanate.

As the method of polymerizing (A) the crosslinked polymer, a conventionally known method and the like can be used, and a solution polymerization method, an emulsion polymerization method, a suspension polymerization method, and a reversed-phase suspension polymerization method can be used. In addition, the polymerization liquid at the polymerization may be in a form of a thin film, mist, or the like. As the method of controlling the polymerization, an adiabatic polymerization method, a temperature-controlled polymerization method, an isothermal polymerization method, and the like can be used. When the suspension polymerization method or the reversed-phase suspension polymerization method is employed as the polymerization method, a conventionally known dispersant, a protective colloid, and the like can be used where necessary. In addition, in the case of employing the reversed-phase suspension polymerization method, polymerization can be conducted by using a solvent such as hexane. As the polymerization method, the solution polymerization method is preferred, and an aqueous solution polymerization method is more preferred since an organic solvent or the like is not used and it is advantageous in terms of production cost.

A water-containing gel {consisting of the crosslinked polymer and water} obtained by the polymerization can be chopped where necessary. The size (largest diameter) of the chopped gel is preferably in a range from 50 µm to 10 cm. If the size falls within the range, dryability at a drying process becomes further favorable. The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains an organic solvent, the content (mass %) of the organic solvent after the removal by distillation is preferably in a range from 0 mass % to 10 mass %, with respect to the mass (100 mass %) of the crosslinked polymer. If the content of the organic solvent falls within the above range, the absorption performance (in particular, water retaining capacity) of the water absorbent resin powder becomes further favorable.

As the method of removing the solvent (including water) by distillation, a method in which removal by distillation (drying) is conducted by hot air at a temperature in a range from 80° C. to 230° C.; a thin film drying method with a drum dryer or the like heated to a temperature in a range from 100° C. to 230° C.; a (heating) reduced-pressure drying method; a freeze-drying method; a drying method with infrared ray; a decantation method; a filtration method; and the like can be used.

(A) The crosslinked polymer can be pulverized after being dried. The pulverizing method is not particularly limited, and for example, an ordinary pulverizing apparatus such as a hammer type pulverizer, an impact type pulverizer, a roll type pulverizer, and a jet streaming type pulverizer can be used. The particle size of (A) the pulverized crosslinked polymer can be adjusted by sieving or the like where necessary. The weight average particle size (µm) of (A) the crosslinked polymer is preferably in a range from 100 µm to 800 µm. If the weight average particle size (µm) of (A) the crosslinked polymer falls within the above range, the absorption performance thereof becomes further favorable. It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21).

(A) The crosslinked polymer can be subjected to surface crosslinking where necessary. As the crosslinking agent (surface crosslinking agent) for conducting the surface crosslinking, the same one as (b) the internal crosslinking agent can be used. In light of absorption performance and the like of the water absorbent resin powder, as the surface crosslinking agent, (b3) the crosslinking agent is preferred, the polyvalent glycidyl is more preferred, ethylene glycol diglycidyl ether or glycerin diglycidyl ether is even more preferred, and ethylene glycol diglycidyl ether is most preferred.

(A) The crosslinked polymer may be one kind, or a mixture of two or more kinds. (A) The crosslinked polymer may be further treated with (B) a surface modifier. Examples of (B) the surface modifier include a polyvalent metal compound such as aluminum sulfate, potassium alum, ammonium alum, sodium alum, (poly)aluminum chloride, and hydrates thereof; a polycation compound such as polyethyleneimine, polyvinylamine, and polyallylamine; an inorganic fine particle; (B1) a surface modifier containing a hydrocarbon group; (B2) a surface modifier containing a hydrocarbon group having a fluorine atom; and (B3) a surface modifier having a polysiloxane structure.

Examples of the inorganic fine particle include an oxide such as silicon oxide (silica), aluminum oxide (alumina), iron oxide, titanium oxide, magnesium oxide, and zirconium oxide; a carbide such as silicon carbide and aluminum carbide; a nitride such as titanium nitride; and a complex thereof (e.g., zeolite, talc, etc.). Among them, the oxide is preferred, and silicon oxide is further preferred. The volume average particle size of the inorganic fine particles is preferably in a range from 1 nm to 500 nm, but it is not limited thereto. The specific surface area of the inorganic fine particle is preferably in a range from 20 $m^2/g$ to 4000 $m^2/g$. If the specific surface area falls within the above range, the absorption performance becomes better. It is noted that the specific surface area is measured according to JIS Z8830: 2001 (nitrogen, a volume method, a multipoint method).

The method of treating (A) the crosslinked polymer with (B) the surface modifier is not particularly limited, as long as treatment is conducted such that (B) the surface modifier is present on the surface of (A) the crosslinked polymer. However, in light of controlling the amount of (B) the surface modifier on the surface, it is preferred that (B) the surface modifier is mixed with a dried product of (A) the crosslinked polymer, not with a water-containing gel of (A) the crosslinked polymer or a polymerization liquid prior to the polymerization of (A) the crosslinked polymer. It is noted that it is preferred that the mixing is uniformly conducted.

The shape of the water absorbent resin powder is not particularly limited, and examples thereof include an indefinite crushed shape, a scale shape, a pearl shape, and a rice grain shape. Among them, the indefinite crushed shape is preferred from the standpoint that the powder in such a shape can be well entangled with fibrous materials in applications such as a disposable diaper and there is little possibility of the powder falling off from the fibrous materials.

The water absorbent resin powder preferably has an absorption speed measured by a vortex method of 5 seconds or more, more preferably 7 seconds or more, and preferably has an absorption speed measured by a vortex method of 55 seconds or less, more preferably 53 seconds or less. If the absorption speed exceeds 55 seconds, the body fluid cannot be sufficiently absorbed when large quantity of body fluid is excreted at a high speed at one time. As a result, liquid leakage may occur. The absorption speed is more preferred if it is lower, but if the absorption speed is less than 5 seconds, the stability of the water absorbent resin powder to urine, in particular, its stability to urine under load, may be lowered. The absorption speed measured by the vortex method is evaluated by measuring a time (seconds) taken to absorb the body fluid. Thus, a shorter measured time (seconds) means the water absorbent resin powder has a higher body fluid absorption speed.

The water absorbent resin powder preferably has an absorption ratio of 50 g/g or more and 70 g/g or less. The absorption ratio is more preferably 52 g/g or more, particularly preferably 54 g/g or more, and is more preferably 68 g/g or less, particularly preferably 64 g/g or less. The absorption ratio is a measure indicating how much water the water absorbent resin powder can absorb. If the absorption ratio is 50 g/g or more, absorption capacity can be maintained at a predetermined level by using a small amount of the water absorbent resin powder, and thus it is easy to manufacture a thin absorbent body. In light of prevention of liquid leakage, the absorption ratio is more preferred if it is greater, but the absorption ratio is preferably 70 g/g or less. This is because if the absorption ratio is 70 g/g or less, the stability of the water absorbent resin powder to urine increases.

The water absorbent resin powder preferably has a water retaining capacity of 20 g/g or more and 65 g/g or less. The water retaining capacity is more preferably 22 g/g or more, particularly preferably 24 g/g or more, and is more preferably 63 g/g or less, particularly preferably 61 g/g or less. The water retaining capacity is a measure indicating how much absorbed liquid the water absorbent resin powder can retain. If the water retaining capacity is 20 g/g or more, absorption capacity of the body fluid can be maintained at a predetermined level by using a small amount of the water absorbent resin powder, and thus it is easy to manufacture a thin absorbent body. In light of prevention of liquid leakage, the water retaining capacity is more preferred if it is greater, but the water retaining capacity is preferably 65 g/g or less. This is because if the water retaining capacity is 65 g/g or less, the stability of the water absorbent resin powder to urine increases.

The absorption speed, the absorption ratio, and the water retaining capacity of the water absorbent resin powder can be adjusted by appropriately selecting the composition of (A) the crosslinked polymer, the type of the surface modifier, the particle size of the water absorbent resin powder, the drying condition, and the like.

The water absorbent resin powder may further include an additive such as an antiseptic, a fungicide, an antibacterial, an antioxidant, an ultraviolet absorbent agent, a coloring agent, a perfuming agent, a deodorizer, an inorganic powder, and an organic fibrous material. Examples of the additive include those exemplified in Japanese Patent Publication No. 2003-225565 A and No. 2006-131767 A. When the additive is included, the content (mass %) of the additive is preferably in a range from 0.001 mass % to 10 mass %, more preferably in a range from 0.01 mass % to 5 mass %, even more preferably in a range from 0.05 mass % to 1 mass %, and most preferably in a range from 0.1 mass % to 0.5 mass %, with respect to (A) the crosslinked polymer (100 mass %).

The mass per unit area of the water absorbent resin powder in the absorbent article is preferably 50 g/m$^2$ or more, more preferably 75 g/m$^2$ or more, even more preferably 100 g/m$^2$ or more, and is preferably 800 g/m$^2$ or less, more preferably 700 g/m$^2$ or less, even more preferably 600 g/m$^2$ or less. If the mass per unit area is 50 g/m$^2$ or more, the strength of the absorption body further increases. If the mass per unit area is 600 g/m$^2$ or less, the texture of the absorbent body is soft.

Next, the structure of the absorbent article according to the present invention will be described. Examples of the structure of the absorbent article according to the present invention include: (1) an embodiment where the absorbent article comprises an absorbent body, a top sheet disposed on a skin surface side of the absorbent body, and a back sheet disposed on an external surface side of the absorbent body, and the top sheet is the fumaric acid-supported sheet; (2) an embodiment where the absorbent article comprises an absorbent body, a top sheet disposed on a skin surface side of the absorbent body, a back sheet disposed on an external surface side of the absorbent body, and an intermediate sheet disposed between the absorbent body and the top sheet, and the intermediate sheet is the fumaric acid-supported sheet; and (3) an embodiment where the absorbent article comprises an absorbent body, a top sheet disposed on a skin surface side of the absorbent body, and a back sheet disposed on an external surface side of the absorbent body, and the absorbent body is wrapped by the fumaric acid-supported sheet.

Next, specific examples of the absorbent article according to the present invention will be described. Examples of the absorbent article according to the present invention include an absorbent article used for absorbing the body fluid discharged from the human body, such as an incontinence pad, a disposable diaper, a sanitary napkin.

When the absorbent article is an incontinence pad or a sanitary napkin, for example, the absorbent body, and where necessary an intermediate sheet are disposed between a liquid permeable top sheet and a liquid impermeable back sheet. The top sheet and/or the intermediate sheet is the fumaric acid-supported sheet. Examples of the shape of the incontinence pad or the sanitary napkin include a substantially rectangular shape, an hourglass shape, a gourd shape, and the like. In addition, a liquid impermeable side sheet may be formed on both sides of the liquid permeable top sheet in the width direction, where necessary. The side sheet is joined to the upper surface of both sides of the top sheet in the width direction, and the side sheet inward of the joining point in the width direction forms one pair of rise flaps along both side edges of the absorbent body.

The liquid permeable top sheet and the intermediate sheet are a liquid permeable sheet material, and are, for example, a nonwoven fabric formed from a hydrophilic fiber. The liquid permeable top sheet and the intermediate sheet quickly capture the body fluid from the wearer, and transfer the body fluid to the absorbent body. The nonwoven fabric used as the top sheet is, for example, a point-bonded nonwoven fabric, an air-through nonwoven fabric, a spunlace nonwoven fabric, or a spunbond nonwoven fabric. As the hydrophilic fiber forming the nonwoven fabric, cellulose, rayon, cotton, and the like are generally used. It is noted that as the top sheet, a liquid permeable nonwoven fabric that is formed from a hydrophobic fiber (e.g., polypropylene, polyethylene, polyester, polyamide, and nylon) whose surface is hydrophilized with a surfactant may be used.

As the liquid impermeable sheet used for the back sheet and the side sheet, a water-repellent or liquid impermeable nonwoven fabric (e.g., a spunbond nonwoven fabric, a meltblown nonwoven fabric, and an SMS (spunbond-meltblown-spunbond) nonwoven fabric) formed from a hydrophobic fiber (e.g., polypropylene, polyethylene, polyester, polyamide, and nylon), or a water-repellent or liquid impermeable plastic film is used. The back sheet and the side sheet prevent the body fluid that reaches the liquid impermeable sheet, from oozing out of the absorbent article. If a plastic film is used as the liquid impermeable sheet, a moisture-permeable (air-permeable) plastic film is preferably used from the standpoint that humid feeling is prevented to improve the wearer's comfort. In addition, a paper sheet may be disposed between the plastic film and the absorbent body to provide better diffusion and shape stability.

When the absorbent article is a disposable diaper, examples of the disposable diaper include: a spreading-type disposable diaper that has one pair of securing members on left and right sides of a back portion or a front abdominal portion, and that forms a pants shape with the securing members when being worn; and a pants-type disposable diaper having a waist opening and one pair of leg openings formed by joining a front abdominal portion and a back portion together.

When the absorbent article is a disposable diaper, in the disposable diaper, for example, a laminated body including an inner sheet and an outer sheet may form a diaper main body including a front abdominal portion, a back portion, and a crotch portion located between those, and the water absorbent layer may be disposed on the crotch portion. Furthermore, the disposable diaper may include, for example, a laminated body having the absorbent body disposed between a top sheet and a back sheet, and the laminated body may include a front abdominal portion, a back portion, and a crotch portion located between those. It is noted that, with regard to the front abdominal portion, the back portion, and the crotch portion, when the disposable diaper is worn, a portion placed on the abdominal side of the wearer is referred to as a front abdominal portion, a portion placed on the hip side of the wearer is referred to as a back portion, and a portion located between the front abdominal portion and the back portion and placed on the crotch of the wearer is referred to as a crotch portion. The inner sheet is preferably hydrophilic or water-repellent, and the outer sheet is preferably water-repellent.

The absorbent article preferably has rise flaps disposed along both side edge portions of the absorbent body. The rise flaps, for example, may be disposed on both side edge portions of the top surface of the absorbent body in the width direction, or may be disposed on both outer sides of the absorbent body in the width direction. By providing the rise flaps, side leakage of the body fluid can be prevented. The rise flaps may be formed by causing inward edges of side sheets provided on both sides of the top sheet in the width direction, to rise. The rise flaps and the side sheets are preferably water-repellent.

Next, the absorbent article according to the present invention will be described with reference to figures. However, the present invention is not limited to the embodiments shown in these figures.

Figure 1:
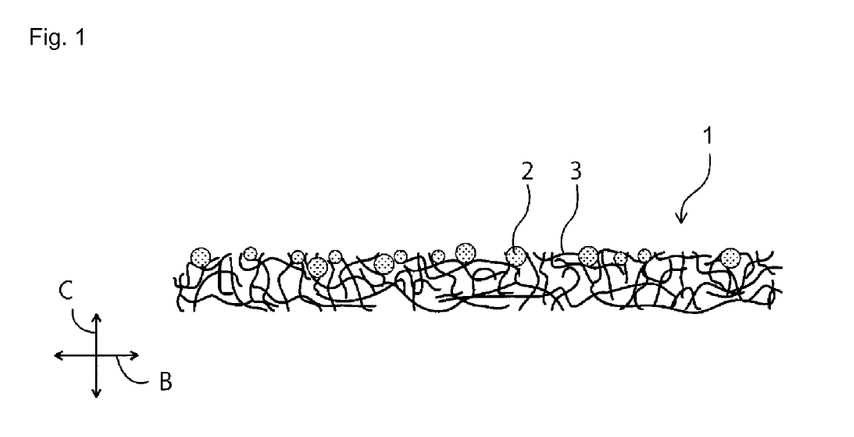
FIG. 1 is a schematic cross sectional view of a fumaric acid-supported sheet.
Figure 2:
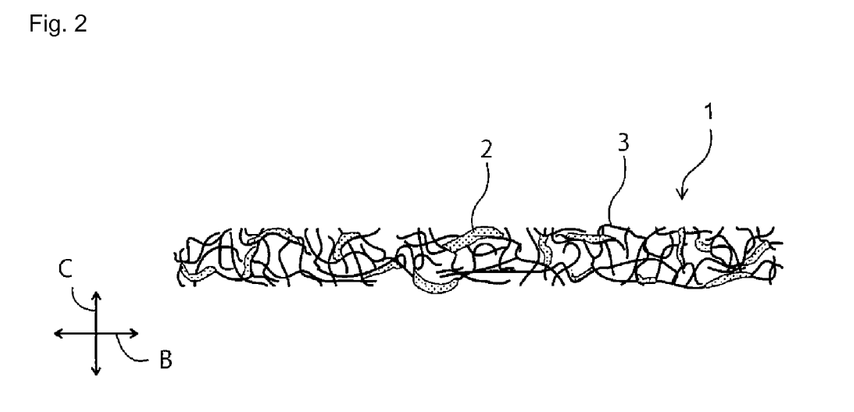
FIG. 2 is a schematic cross sectional view of another fumaric acid-supported sheet.

FIG. 1 and FIG. 2 are a schematic cross sectional view showing an embodiment of a fumaric acid-supported sheet. In FIG. 1 and FIG. 2, with respect to C direction on the paper surface, the upper side is the skin surface side, and the lower side is the external surface side. In the fumaric acid-supported sheet 1 shown in FIG. 1, particles of fumaric acid 2 having an average particle diameter of 30 μm or less are supported by fibers 3 constituting a base material sheet. In the fumaric acid-supported sheet 1 shown in FIG. 1, particles of fumaric acid 2 may be coated with a dispersant (not shown in the figure). In the fumaric acid-supported sheet 1 shown in FIG. 2, at least a part of fibers 3 constituting a base material sheet is coated with fumaric acid 2.

Figure 3:
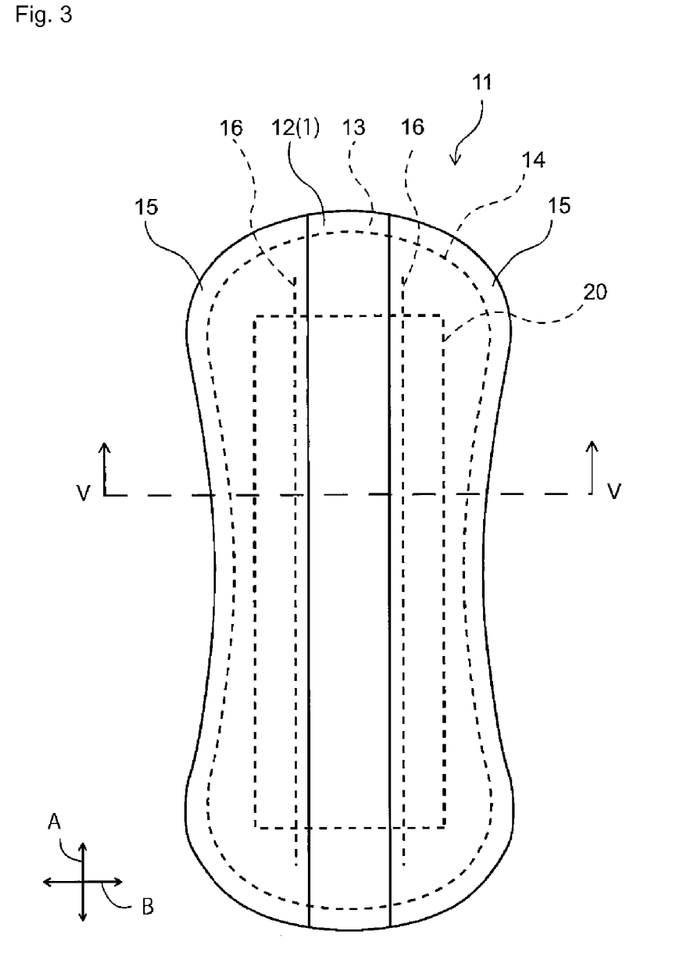
FIG. 3 is a planar view of an absorbent article according to the present invention.
Figure 4:
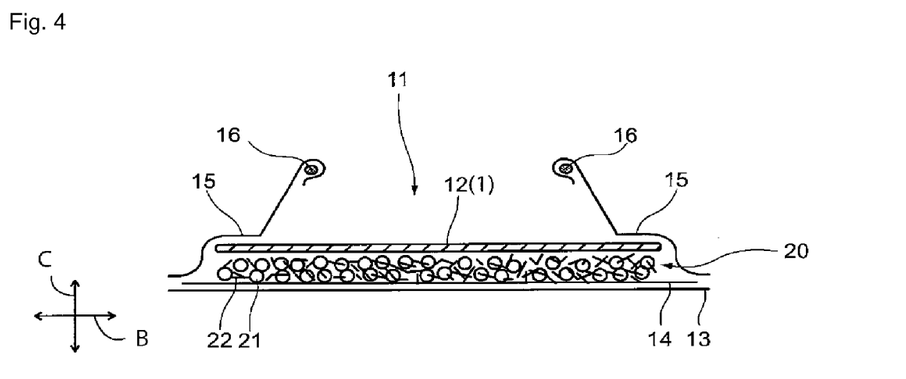
FIG. 4 is a schematic cross sectional view along line V-V in FIG. 3.

FIG. 3 shows an incontinence pad that is an embodiment of an absorbent article according to the present invention. FIG. 3 shows a planar view of the incontinence pad. FIG. 4 shows a cross sectional view along line V-V of the incontinence pad in FIG. 3. It is noted that in these figures, arrow B is defined as a width direction, and arrow A is defined as a longitudinal direction. Furthermore, a direction on the surface formed by arrows A and B is defined as a planar direction.

The incontinence pad 11 comprises a liquid permeable top sheet 12, a liquid impermeable back sheet 13, and an absorbent body 20 disposed therebetween. The absorbent body 20 is formed by fixing a water absorbent resin powder 21 and a fiber base material 22 to a tissue paper 14. The top sheet 12 is the fumaric acid-supported sheet 1.

The top sheet 12 is disposed so as to face the skin at the crotch portion of the wearer, and allows the body fluid from the wearer to pass through. The body fluid that has passed through the top sheet 12 is taken into the absorbent body 20, and then absorbed by the water absorbent resin powder 21. Fumaric acid 2 (not shown in the figure) is water-insoluble, so fumaric acid 2 is not immediately but slowly dissolved into the body fluid. As a result, even after the water absorbent resin powder 21 has absorbed the body fluid or the like, alkalization of the top sheet 12 can be prevented over a long period of time.

Side sheets 15 extending in the longitudinal direction A of the incontinence pad 11 are joined on both side edges of the top sheet 12 in the width direction B. The side sheets 15 are formed from a liquid impermeable plastic film, a water-repellent nonwoven fabric, or the like. The side sheets 15 have rise elastic members 16 disposed at inward edges of the incontinence pad 11 in the width direction. When the incontinence pad 11 is used, the inward edges of the side sheets 15 rise toward the wearer's skin through contractive force of the rise elastic members 16 to prevent side leakage of the body fluid.

Figure 5:
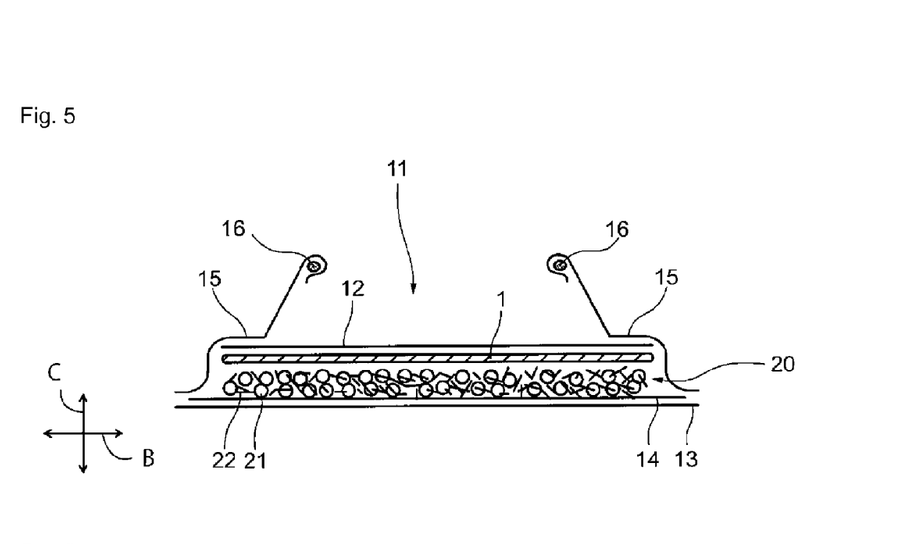
FIG. 5 is a schematic cross sectional view of another absorbent article according to the present invention.

FIG. 5 shows a schematic cross sectional view of another absorbent article according to the present invention. In the incontinence pad shown in FIG. 5, as an intermediate sheet, a fumaric acid-supported sheet 1 is disposed between a liquid permeable top sheet 12 and an absorbent body 20. FIG. 5 shows an embodiment where the intermediate sheet is the fumaric acid-supported sheet 1, however, both of the intermediate sheet and the top sheet 12 may be the fumaric acid-supported sheet 1. Furthermore, FIG. 4 and FIG. 5 show the absorbent body 20 is formed by fixing the water absorbent resin powder 21 and the fiber base material 22 to the tissue paper 14, however, the water absorbent resin powder 21 and the fiber base material 22 may be wrapped with the tissue paper 14.

Figure 6:
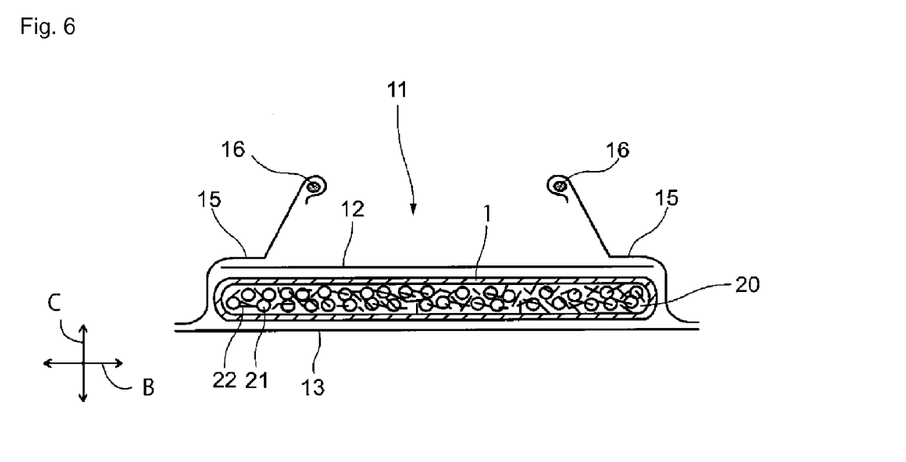
FIG. 6 is a schematic cross sectional view of another absorbent article according to the present invention.

FIG. 6 shows a schematic cross sectional view of another absorbent article according to the present invention. In the incontinence pad shown in FIG. 6, an absorbent body 20 comprising a water absorbent resin powder 21 and a fiber base material 22 is wrapped with a fumaric acid-supported sheet 1. FIG. 6 shows an embodiment where the liquid permeable sheet wrapping the absorbent body 20 is the fumaric acid-supported sheet 1, however, a top sheet 12 may also be the fumaric acid-supported sheet 1, and furthermore the fumaric acid-supported sheet 1 may be disposed as the intermediate sheet. FIG. 4 to FIG. 6 show an embodiment where the absorbent body 20 comprises one water absorbent layer, however, the absorbent body 20 may comprise multiple water absorbent layers. In addition, FIG. 4 to FIG. 6 show an embodiment where the absorbent article 11 comprises one absorbent body 20, however, the absorbent article 11 may comprise two or more absorbent bodies 20. For the same constituent members in FIG. 5 and FIG. 6 as those in FIG. 4, the explanations about the same symbols thereof are abbreviated.

Specific examples of the absorbent article according to the present invention include an absorbent article used for absorbing the body fluid discharged from the human body, such as a disposable diaper, a sanitary napkin, and an incontinence pad.

EXAMPLE

Hereinafter, the present invention will be described in detail by means of examples. However, the present invention is not limited to the following examples, any change and embodiment that do not depart from the gist of the present invention are included in the scope of the present invention.
[Evaluation Methods]
(Method of Measuring Water Absorption Speed by Vortex Method)

50 mL of a saline (0.9 mass % sodium chloride aqueous solution) and a magnetic stir tip (a diameter at center portion: 8 mm, a diameter at both end portions: 7 mm, length: 30 mm, the surface was coated with a fluororesin) were placed into a 100 mL glass beaker, and the beaker was placed on a magnetic stirrer ("HPS-100" manufactured by AS ONE Corporation). The rotational speed of the magnetic stirrer was adjusted to 600 plus or minus 60 rpm, and the saline was stirred. 2.0 g of a sample was added to the solution at the center of the vortex of the saline being stirred, and the water absorption speed (seconds) of the water absorbent resin powder was measured according to JIS K 7224 (1996). Specifically, a stopwatch was started at the time when the addition of the water absorbent resin powder that was the sample, to the beaker was completed. The stopwatch was stopped at the time when the stirrer tip was covered with the test solution (the time when the vortex disappeared and the solution surface became flat), and the time (seconds) was recorded as a water absorption speed. The measurement was conducted five times (n=5), the highest and lowest values were removed, and the average of the remaining three values was regarded as a measured value. It is noted that these measurements were conducted at 23° C. plus or minus 2° C. and a relative humidity of 50% plus or minus 5%, and samples were stored in the same environment for 24 hours or longer prior to the measurements and then were subjected to the measurements.
(Method of Measuring Absorption Ratio)

Measurement of an absorption ratio was conducted according to JIS K 7223 (1996). A nylon mesh having openings of 63 μm (JIS Z8801-1: 2000) was cut into a rectangle having a width of 10 cm and a length of 40 cm and folded in half at a center in its longitudinal direction, and both ends thereof were heat sealed, to produce a nylon bag having a width of 10 cm (inside dimension: 9 cm) and a length of 20 cm. 1.00 g of a measurement sample was precisely weighted and placed into the produced nylon bag such that the sample was uniform at the bottom of the nylon bag. The nylon bag containing the sample was immersed in a saline. After 60 minutes from start of the immersion, the nylon bag was taken out from the saline, and was hung vertically for one hour to drain the nylon bag. Then, the mass (F1) of the sample was measured. In addition, the same operation was conducted without using any sample, and a mass F0 (g) at that time was measured. Then, an absorption ratio which was an object was calculated according to the following equation from these masses F1 and F0 and the mass of the sample.

Absorption ratio (g/g)=(F1−F0)/mass of sample (Method of Measuring Water Retaining Capacity)

Measurement of a water retaining capacity was conducted according to JIS K 7223 (1996). A nylon mesh having openings of 63 μm (JIS Z8801-1: 2000) was cut into a rectangle having a width of 10 cm and a length of 40 cm and folded in half at a center in its longitudinal direction, and both ends thereof were heat sealed, to produce a nylon bag having a width of 10 cm (inside dimension: 9 cm) and a length of 20 cm. 1.00 g of a measurement sample was precisely weighted and placed into the produced nylon bag such that the sample was uniform at the bottom of the nylon bag. The nylon bag containing the sample was immersed in a saline. After 60 minutes from start of the immersion, the nylon bag was taken out from the saline, and was hung vertically for one hour to drain the nylon bag. Then, the nylon bag was dehydrated using a centrifugal hydroextractor (model H-130C special type manufactured by Kokusan Co., Ltd.). The dehydrating conditions were 143 G (800 rpm) and 2 minutes. A mass R1 (g) after the dehydration was measured. In addition, the same operation was conducted without using any sample, and a mass R0 (g) at that time was measured. Then, a water retaining capacity which was an object was calculated according to the following equation from these masses R1 and R0 and the mass of the sample.

Water retaining capacity (g/g)=(R1−R0−mass of sample)/mass of sample (Skin Stimulation and Malodor Intensity)

5 ml of urine was allowed to be absorbed separately in three times by an absorbent article which was formed to a size having a width of 5 cm and a length of 5 cm. The absorbent article having absorbed urine was attached on the inside of the test subject's thigh in a manner that the top sheet (liquid permeable nonwoven fabric) thereof was in contact with the test subject' skin, and left for 16 hours. After 16 hours, the absorbent article was peeled off, and the state of the skin at the position where the absorbent article had been attached was visually observed and evaluated according to the following five-grade scoring. In addition, malodor intensity of the absorbent article which had been peeled off was evaluated according to the following six-grade scoring. Each of the evaluations was conducted by twenty test subjects, and an average value of the evaluation results of the twenty test subjects was used as an evaluation result of that absorbent article.
<Skin Stimulation Evaluation Criteria>
  5: no change
  4: little change
  3: reddish
  2: red
  1: rash <Malodor Intensity Evaluation Criteria>

0: odorless

1: little perceivable odor

2: a litter perceivable but weak odor

3: easily perceivable odor

4: strong odor

5: very strong odor

[Production of Laminated Product]

A synthetic rubber hotmelt adhesive was applied to a liquid impermeable sheet, and a tissue paper was laminated thereon. A synthetic rubber hotmelt adhesive was applied to the tissue paper, and then a mixture including pulp and a water absorbent resin powder ("Aqua Pearl (registered trademark)" DS560, manufactured by San-Dia Polymers, Ltd.) was spread thereon (mass per unit area of the water absorbent resin powder: 100 g/m$^2$) to obtain a water absorbent layer. A synthetic rubber hotmelt adhesive was applied to the water absorbent layer, and a tissue paper was laminated thereon. A synthetic rubber hotmelt adhesive was further applied to the tissue paper, and a liquid permeable nonwoven fabric was laminated thereon to obtain a laminated product. The physical properties of the water absorbent resin powder were as follows, absorption ratio: 60 g/g, water retaining capacity: 42 g/g, water absorption speed by vortex method: 38 s.

[Production of Absorbent Article]

Absorbent Article 1

A mixed liquid containing 47.5 g of distilled water at the room temperature, and 12.5 g of CARRYBON (registered trademark) B (polycarboxylic acid (salt) type dispersant, solid component content: 40 mass %, manufactured by Sanyo Chemical Industries Co. Ltd) which was a dispersant, was prepared. 40 g of fumaric acid was added into the mixed liquid, and pulverized and dispersed by using a homogenizer (Biomixer BM-2, manufactured by Nihonseiki Kaisha Ltd.) until fumaric acid particles had a volume average particle diameter of 2 μm. Distilled water was added into the above liquid to obtain a fumaric acid dispersion liquid in which the fumaric acid concentration was adjusted to 0.1 mass %. The dispersant content was 12.5 parts by mass with respect to 100 parts by mass of fumaric acid. The volume average particle diameter of fumaric acid in the dispersion liquid was measured using a laser diffraction scattering type particle size analyzer (MT300011, manufactured by Nikkiso Co., Ltd). The fumaric acid dispersion liquid was applied to the liquid permeable nonwoven fabric (top sheet) of the laminated product by using a spray, and drying was conducted to obtain Absorbent article 1. The applied amount of the fumaric acid dispersion liquid was adjusted such that the liquid permeable nonwoven fabric of Absorbent article 1 had a fumaric acid-supporting amount of 1.0 g/m$^2$. The top sheet of Absorbent article 1 was a sheet which supported fumaric acid particles having an average particle diameter of 30 μm or less.

Absorbent Articles 2-12

Absorbent articles 2-12 were obtained in the same manner as that in Absorbent article 1, except that the type or the volume average particle diameter of the acid compound was changed according to Table 1.

Absorbent Article 13

Absorbent article 13 was obtained in the same manner as that in Absorbent article 1, except that fumaric acid was not used.

Skin stimulation and malodor intensity evaluation results of Absorbent articles 1-13 are shown in Table 1.

TABLE 1

| | Acid compound | Average particle diameter (μm) | Supporting amount (g/m$^2$) | Skin stimulation | | Malodor intensity | |
|---|---|---|---|---|---|---|---|
| | | | | Score | Evaluation | Score | Evaluation |
| Absorbent article 1 | Fumaric acid | 2 | 1.0 | 4.8 | Excellent | 2.2 | Excellent |
| Absorbent article 2 | Fumaric acid | 8 | 1.0 | 4.5 | Excellent | 2.4 | Excellent |
| Absorbent article 3 | Fumaric acid | 28 | 1.0 | 4.4 | Excellent | 2.5 | Excellent |
| Absorbent article 4 | Adipic acid | 8 | 1.0 | 3.9 | Good | 3.0 | Good |
| Absorbent article 5 | Succinic acid | 9 | 1.0 | 3.8 | Good | 3.2 | Good |
| Absorbent article 6 | Itaconic acid | 8 | 1.0 | 3.8 | Good | 3.3 | Good |
| Absorbent article 7 | Benzoic acid | 9 | 1.0 | 3.7 | Good | 3.1 | Good |
| Absorbent article 8 | Silica | 0.05 | 1.0 | 3.5 | Good | 3.4 | Good |
| Absorbent article 9 | Fumaric acid | 35 | 1.0 | 2.7 | Poor | 4.1 | Poor |
| Absorbent article 10 | Adipic acid | 33 | 1.0 | 2.6 | Poor | 4.0 | Poor |
| Absorbent article 11 | Lactic acid | (Dissolved) | 1.0 | 2.3 | Poor | 4.6 | Poor |
| Absorbent article 12 | Citric acid | (Dissolved) | 1.0 | 2.3 | Poor | 4.4 | Poor |
| Absorbent article 13 | — | — | — | 2.1 | Poor | 4.5 | Poor |

As apparent from Table 1, Absorbent articles 1-3 on which fumaric acid having an average particle diameter of 30 μm or less was supported, show weak skin stimulation since the top sheet thereof was retained to weak acidity by fumaric acid. Furthermore, Absorbent articles 1-3 also show weak malodor intensity since proliferation of putrefactive bacteria was inhibited.

On the contrary, Absorbent article 9 on which fumaric acid having an average particle diameter larger than 30 μm was supported, shows strong skin stimulation and strong malodor intensity, thus the fumaric acid-supported effect is not sufficiently imparted thereto. In the case such as Absorbent articles 4 to 8 where the average particle diameter of adipic acid, succinic acid, itaconic acid, benzoic acid, and silica was adjusted to 30 μm or less, suppression effect in skin stimulation and malodor intensity is small. In addition, in the case such as Absorbent articles 11 and 12 where lactic acid or citric acid was used, skin stimulation evaluation was at the same level as that of Absorbent article 13 which did not use the acid compound, since the acid compound was dissolved in urine such that it was not retained in the top sheet.

Absorbent Article 14

A mixed liquid containing 47.5 g of distilled water at the room temperature, and 12.5 g of CARRYBON (registered trademark) B (polycarboxylic acid (salt) type dispersant, solid component content: 40 mass %, manufactured by Sanyo Chemical Industries Co. Ltd) which was a dispersant, was prepared. 40 g of fumaric acid was added into the mixed liquid, and pulverized by using a homogenizer (Biomixer BM-2, manufactured by Nihonseiki Kaisha Ltd.) until fumaric acid particles had a volume average particle diameter of 8 μm. Water was removed from the dispersion liquid to obtain a fumaric acid particle powder having a volume average particle diameter of 8 μm. The fumaric acid particles were spread on the liquid permeable nonwoven fabric (top sheet) of the laminated product to obtain Absorbent article 14. The spread amount of the fumaric acid particles was adjusted such that the liquid permeable nonwoven fabric of Absorbent article 14 had a fumaric acid-supporting amount of 1.0 g/m². The top sheet of Absorbent article 14 was a sheet which supported fumaric acid particles having an average particle diameter of 30 μm or less.

Skin stimulation and malodor intensity evaluation results of Absorbent article 14 are shown in Table 2. Evaluation results of Absorbent article 2 are also shown in Table 2 for comparison. In addition, in order to compare supporting property of fumaric acid particles, skin stimulation and malodor intensity of Absorbent articles 2 and 14 which had been subjected to shaking treatment were also evaluated. The shaking treatment was conducted by placing the absorbent article on a sanitary sieve shaker (SF-300, manufactured by Sansho Industry Co., Ltd.) in a manner that the top sheet of the absorbent article was upside down, and shaking the absorbent article for one minute.

malodor intensity evaluation results before and after the shaking treatment, whereas Absorbent article 14 shows inferior skin stimulation and malodor intensity evaluation results after the shaking treatment. It is considered that this is because the fumaric acid particles fell off due to the shaking treatment. Therefore, it is apparent that the fumaric acid particles which were supported by applying the fumaric acid dispersion liquid to the supporting member, show larger supporting strength.

Absorbent Article 15

1.0 g of fumaric acid was added into 200 g of a warm water whose temperature was adjusted to 50° C., and the mixed liquid was stirred using a magnetic supersonic wave stirrer USS-2 (manufactured by Nihonseiki Kaisha Ltd.) to completely dissolve fumaric acid such that a fumaric acid solution 1 was obtained. The fumaric acid solution 1 was applied to the liquid permeable nonwoven fabric (top sheet) of the laminated product by using a spray, and drying was conducted to obtain Absorbent article 15. The applied amount of the fumaric acid solution 1 was adjusted such that the liquid permeable nonwoven fabric of Absorbent article 15 had a fumaric acid-supporting amount of 1.0 g/m². The top sheet of Absorbent article 15 was a sheet in which at least a part of constituent fibers were coated with fumaric acid.

Absorbent Article 16

1.0 g of fumaric acid was added into 200 g of ethanol (purity: at least 95%) whose temperature was adjusted to 30° C., and the mixed liquid was stirred using a magnetic supersonic wave stirrer USS-2 (manufactured by Nihonseiki Kaisha Ltd.) to completely dissolve fumaric acid such that a fumaric acid solution 2 was obtained. The fumaric acid solution 2 was applied to the liquid permeable nonwoven

TABLE 2

| | | Dispersant | | | Skin stimulation | | Malodor intensity | |
|---|---|---|---|---|---|---|---|---|
| | Supporting method | Type | Amount (parts by mass*) | | Score | Evaluation | Score | Evaluation |
| Absorbent article 2 | Applying | Polycarboxylic acid (salt) type dispersant | 12.5 | Before shanking | 4.5 | Excellent | 2.4 | Excellent |
| | | | | After shanking | 4.5 | Excellent | 2.4 | Excellent |
| Absorbent article 14 | Spreading | Polycarboxylic acid (salt) type dispersant | 12.5 | Before shanking | 4.4 | Excellent | 2.5 | Excellent |
| | | | | After shanking | 3.1 | Good | 3.0 | Good |

*Amount with respect to 100 parts by mass of fumaric acid particles

Absorbent article 2 was obtained by applying the fumaric acid dispersion liquid to the liquid permeable nonwoven fabric for supporting the fumaric acid particles. Absorbent article 14 was obtained by spreading the fumaric acid particle powder to the liquid permeable nonwoven fabric for supporting the fumaric acid particles. Absorbent articles 2 and 14 before the shaking treatment show nearly same skin stimulation and malodor intensity evaluation results. It is apparent from the above results that skin stimulation and malodor intensity suppression effect imparted by fumaric acid is not affected by the supporting method. However, Absorbent article 2 shows unchanged skin stimulation and fabric (top sheet) of the laminated product by using a spray, and drying was conducted to obtain Absorbent article 16. The applied amount of the fumaric acid solution 2 was adjusted such that the liquid permeable nonwoven fabric of Absorbent article 16 had a fumaric acid-supporting amount of 1.0 g/m². The top sheet of Absorbent article 16 was a sheet in which at least a part of constituent fibers were coated with fumaric acid.

Skin stimulation and malodor intensity evaluation results of Absorbent articles 15 and 16 are shown in Table 3. In addition, Evaluation results of Absorbent article 1 are also shown in Table 3 for comparison.

TABLE 3

| | Acid compound-containing liquid | | Supporting amount | Skin stimulation | | Malodor intensity | |
|---|---|---|---|---|---|---|---|
| | Form | Solvent | (g/m²) | Score | Evaluation | Score | Evaluation |
| Absorbent article 1 | Dispersion liquid | Water (RT) | 1.0 | 4.8 | Excellent | 2.2 | Excellent |
| Absorbent article 15 | Solution | Water (50° C.) | 1.0 | 4.8 | Excellent | 2.0 | Excellent |
| Absorbent article 16 | Solution | Ethanol (30° C.) | 1.0 | 4.9 | Excellent | 2.1 | Excellent |

Absorbent articles 15 and 16 were obtained by contacting the sheet base material with the fumaric acid-containing liquid in which fumaric acid was dissolved, and then removing the solvent to coat a least a part of the fibers constituting the sheet base material with fumaric acid. Absorbent articles 15 and 16 show nearly same skin stimulation and malodor intensity evaluation results as Absorbent article 1. It is apparent from the above results that a warm water, a hydrophilic organic solvent or the like, which can dissolve fumaric acid, can be employed as the solvent of the fumaric acid-containing liquid.

INDUSTRIAL APPLICABILITY

The absorbent article according to the present invention is suitably used as, for example, an absorbent article for absorbing the body fluid discharged from the human body, and in particular, is suitably used as an absorbent article such as an incontinence pad, a disposable diaper, and a sanitary napkin.

REFERENCE SIGNS LIST

1: fumaric acid-supported sheet, 2: fumaric acid, 3: fiber, 11: incontinence pad (absorbent article), 12: top sheet, 13: back sheet, 14: tissue paper, 15: side sheet, 16: rise elastic member, 17: intermediate sheet, 20: absorbent body, 21: water absorbent resin powder, 22: fiber base material

The invention claimed is:

1. An absorbent article comprising an absorbent body, and a fumaric acid-supported sheet disposed on a skin surface side of the absorbent body,
   wherein the fumaric acid-supported sheet is a sheet supporting fumaric acid particles having an average particle diameter of 30 μm or less, and/or a sheet in which at least a part of constituent fibers is coated with fumaric acid,
   the absorbent body includes a water absorbent resin powder, and
   a ratio (supporting amount of fumaric acid/mass per unit area of water absorbent resin powder) of a supporting amount of fumaric acid on the fumaric acid-supporting sheet (g/m²) to a mass per unit area of the water absorbent resin powder in the absorbent article (g/m²) is in a range from 0.001 to 20.

2. The absorbent article according to claim 1, wherein at least a part of a particle surface of the fumaric acid particles is coated with a dispersant.

3. The absorbent article according to claim 2, wherein the dispersant is at least one selected from the group consisting of an anionic high molecular type dispersant, an anionic surfactant type dispersant, and a nonionic surfactant type dispersant.

4. The absorbent article according to claim 2, wherein the dispersant is a polycarboxylic acid (salt) type dispersant.

5. The absorbent article according to claim 2, wherein an amount of the dispersant is in a range from 1 part by mass to 50 parts by mass with respect to 100 parts by mass of fumaric acid particles.

6. The absorbent article according to claim 1, wherein the fumaric acid-supported sheet supports fumaric acid in a supporting amount ranging from 0.01 g/m² to 10 g/m².

7. The absorbent article according to claim 1, wherein the absorbent article comprises a top sheet disposed on a skin surface side of the absorbent body, and a back sheet disposed on an external surface side of the absorbent body, and wherein the top sheet is the fumaric acid-supported sheet.

8. The absorbent article according to claim 1, wherein the absorbent article comprises a top sheet disposed on a skin surface side of the absorbent body, a back sheet disposed on an external surface side of the absorbent body, and an intermediate sheet disposed between the absorbent body and the top sheet, and wherein the intermediate sheet is the fumaric acid-supported sheet.

9. The absorbent article according to claim 1, wherein the fumaric acid-supported sheet is obtained by contacting a sheet base material with a fumaric acid-containing liquid containing fumaric acid and a solvent, and then removing the solvent for the sheet base material to support fumaric acid.

10. The absorbent article according to claim 9, wherein the fumaric acid-containing liquid contains a dispersant.

11. The absorbent article according to claim 10, wherein the fumaric acid-containing liquid contains the dispersant in an amount ranging from 1 part by mass to 50 parts by mass with respect to 100 parts by mass of fumaric acid.

12. The absorbent article according to claim 9, wherein the fumaric acid-containing liquid is a fumaric acid particle dispersion liquid or a fumaric acid solution.

13. The absorbent article according to claim 9, wherein the solvent is water and/or a hydrophilic organic solvent.

14. The absorbent article according to claim 9, wherein the fumaric acid-containing liquid contains fumaric acid in an amount ranging from 0.05 mass % to 50 mass %.

15. The absorbent article according to claim 1, wherein the constituent fibers are fibers having a polar group.

16. The absorbent article according to claim 15, wherein the polar group is a hydroxyl group, an ester group, or an ether group.

17. The absorbent article according to claim 1, wherein the mass per unit area of the water absorbent resin powder in the absorbent article is in a range from 50 g/m² to 800 g/m².

18. The absorbent article according to claim 1, wherein the fumaric acid-supported sheet supports fumaric acid in a supporting amount ranging from 0.01 g/m² to 10 g/m², and the fumaric acid-supported sheet is obtained by contacting a sheet base material with a fumaric acid-containing liquid containing fumaric acid and a solvent, and then removing the solvent for the sheet base material to support fumaric acid.

19. The absorbent article according to claim 18, wherein the fumaric acid-supported sheet is a sheet supporting fumaric acid particles having an average particle diameter of 30 μm or less, and the fumaric acid-containing liquid is a fumaric acid particle dispersion liquid.

20. The absorbent article according to claim 18, wherein the fumaric acid-supported sheet is a sheet in which at least a part of constituent fibers is coated with fumaric acid, and the fumaric acid-containing liquid is a fumaric acid solution.

* * * * *